United States Patent
Sarrafzadeh et al.

(10) Patent No.: US 10,265,029 B2
(45) Date of Patent: Apr. 23, 2019

(54) METHODS AND SYSTEMS FOR CALCULATING AND USING STATISTICAL MODELS TO PREDICT MEDICAL EVENTS

(71) Applicant: THE REGENTS OF THE UNIVERSITY OF CALIFORNIA, Oakland, CA (US)

(72) Inventors: Majid Sarrafzadeh, Anaheim, CA (US); Myung-Kyung Suh, Los Angeles, CA (US); Mars Lan, Los Angeles, CA (US); Hassan Ghasemzadeh, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/424,946

(22) PCT Filed: Aug. 28, 2013

(86) PCT No.: PCT/US2013/057137
§ 371 (c)(1),
(2) Date: Feb. 27, 2015

(87) PCT Pub. No.: WO2014/036173
PCT Pub. Date: Mar. 6, 2014

(65) Prior Publication Data
US 2015/0257712 A1    Sep. 17, 2015

Related U.S. Application Data

(60) Provisional application No. 61/694,171, filed on Aug. 28, 2012.

(51) Int. Cl.
*A61B 5/0402*    (2006.01)
*A61B 5/00*    (2006.01)
(Continued)

(52) U.S. Cl.
CPC ........ *A61B 5/7282* (2013.01); *A61B 5/02055* (2013.01); *A61B 5/0402* (2013.01);
(Continued)

(58) Field of Classification Search
CPC ... A61B 5/7282; A61B 5/7264; A61B 5/7267; A61B 5/0476; A61B 5/0402; G06F 19/345
See application file for complete search history.

(56) References Cited

U.S. PATENT DOCUMENTS 6,248,063 B1    6/2001    Barnhill et al.
6,549,804 B1 *  4/2003    Osorio ................... A61B 5/048
                                                            600/300

(Continued)

FOREIGN PATENT DOCUMENTS

JP    2007-066058 A    3/2007
JP    2007-534086 A    11/2007
(Continued)

OTHER PUBLICATIONS

Anonymous: "Dimensionality reduction", Apr. 13, 2016, Retrieved from the Internet: URL: https://en.wikipedia.org/wiki/Dimensionality_reduction [retrieved on Apr. 14, 2016].
(Continued)

*Primary Examiner* — George R Evanisko
(74) *Attorney, Agent, or Firm* — Foley & Lardner LLP; Cliff Z. Liu

(57) ABSTRACT

Systems and methods for generalized precursor pattern discovery that work with a wide range of biomedical signals and applications to detect a wide range of medical events are disclosed. In some embodiments, the methods and systems do not require domain-specific knowledge or significant reconfiguration based on the medical event being analyzed, hence it is also possible to discover patterns previously
(Continued)

unknown to experts. In some embodiments, to build precursor pattern detection models, the system obtains annotated monitoring data. Positive and negative segments are extracted from the annotated monitoring data, and are preprocessed. Features are extracted from the preprocessed segments, and selected features are chosen from the extracted features. The selected features are classified to create the precursor pattern detection model The precursor pattern detection model may then be used in real time to detect occurrences of the medical event of interest.

20 Claims, 12 Drawing Sheets

(51) Int. Cl.
  *G06N 99/00* (2019.01)
  *A61B 5/0205* (2006.01)
  *A61B 5/0476* (2006.01)
  *A61B 5/11* (2006.01)
  *G16H 50/20* (2018.01)
  *G06F 19/00* (2018.01)

(52) U.S. Cl.
  CPC ............ *A61B 5/0476* (2013.01); *A61B 5/112* (2013.01); *A61B 5/4094* (2013.01); *A61B 5/4818* (2013.01); *A61B 5/725* (2013.01); *A61B 5/726* (2013.01); *A61B 5/7264* (2013.01); *A61B 5/746* (2013.01); *G06F 19/00* (2013.01); *G06N 99/005* (2013.01); *G16H 50/20* (2018.01); *F04C 2270/041* (2013.01)

(56) References Cited

U.S. PATENT DOCUMENTS

| 7,437,266 B2 | 10/2008 | Ueno et al. |
| 2011/0119212 A1* | 5/2011 | De Bruin ................ A61B 5/00 706/12 |

FOREIGN PATENT DOCUMENTS

| KR | 10-2010-0126365 A | 12/2010 |
| WO | WO-2005/103300 A2 | 11/2005 |
| WO | WO-2009/099379 A1 | 8/2009 |

OTHER PUBLICATIONS

Anonymous: "Mutual information", Apr. 13, 2016, Retrieved from the Internet: URL:https://en.wikipedia.org/wiki/Mutual_information [retrieved on Apr. 14, 2016].
Extended European Search Report and Search Opinion for European Patent Application No. 13832651.7 dated Apr. 25, 2016.
Goldberger et al. (2000), "Physiobank, physiotoolkit, and physionet: Components of a new research resource for complex physiologic signals", Circulation, vol. 101, No. 23, pp. e215-e220.
Lotte F et al. (2007), "Topical Review: A review of classification algorithms for EEG-based brain-computer interfaces", Journal of Neural Engineering, Institute of Physics Publishing, Bristol, GB, vol. 4, No. 2, Jan. 31, 2007, pp. R1-R13.
International Search Report for International Application No. PCT/US2013/057137 dated Dec. 27, 2013.

* cited by examiner

| Algorithm | Description | Parameters |
|---|---|---|
| Naïve Bayes Classifier (NBC) | NBC uses Bayes' theorem and assumes each feature is conditionally independent. The posterior probability of a class C given a set of features F1, F2, ... Fn is therefore $$p(C|F_1, F_2, ..., F_n) \propto p(C) \prod_{i=1}^{n} p(F_i|C)$$ The prior and likelihood can be calculated from the training set directly and applies to the test set. | |
| Nearest Neighbor (kNN) | An unlabeled instance is classified based on its nearest k neighbors from the training set based on majority vote. Euclidean distance of the features is often used to determine the closeness of two instances $$d = \sqrt{\sum_{i=1}^{n}(x_i - y_i)^2}$$ where $x_i$ and $y_i$ are corresponding features from the two instances. | k = 5 |
| Logistic Regression (LR) | Logistic regression is a type of regression that predicts the outcome of a binary depend variable (class) based on a set of independent variables (features) $X_i$ using the logistic function $$p(x) = \frac{1}{1 + e^{-f(x)}}, \quad f(x) = \beta_0 + \beta_1 X_1 + \beta_2 X_2 + ... + \beta_i X_i$$ where $p(x)$ is the probability of $x$ being class 1, given regression coefficients $\beta_1 ... \beta_i$ and intercept $\beta_0$. | |
| Voting Feature Interval (VFI) | VFI classifies builds upper and lower bounds around each class for each feature. Classification is based on majority voting, where a vote for class C based from feature $a$ is computed as $$v(a, C) = \frac{\text{interval\_class\_count}(a, i, C)}{\text{class\_count}(C)} \left( \frac{H(C|a)}{\text{max uncertainty}} \right)^{\text{bias}}$$ | bias = 0.6 |
| Ripple-Down Rule Learner (RIDOR) | RIDOR is a version of Ripple Down Rule using the Indcut algorithm where the default rules are first generated based on least error rate. A set of exception rules are generated to predict classes other than those covered by the default rules. | |
| C4.5 Decision Tree (C4.5) | C4.5 constructs a decision tree based on information entropy. Each feature in the training set is evaluated for its information gain $$IG(T, a) = H(T) - H(T|a) \quad H(T) = -\sum_{i=1}^{n} p(x_i) \ln p(x_i)$$ Feature with the largest $IG$ and have yet been used is chosen to split the decision tree at each node until the confidence falls below certain threshold. | confidence = 0.25 |

*Fig.5.*

|  | CHBMIT | APNEA-ECG | MIMIC II |
|---|---|---|---|
| NAÏVE | 77.8% | 81.5% | 78.7% |
| BAYES NETWORK | 79.8% | 80.6% | 79.3% |
| LOGISTIC REGRESSION | 76.7% | 79.3% | 75.4% |
| C4.5 | 81.3% | 82.1% | 80.9% |
| SVM | 80.2% | 84.7% | 82.1% |
| VFI | 79.4% | 79.7% | 78.8% |
| ANN | 79.8% | 81.5% | 81.3% |

*Fig. 6.*

|  | CHBMIT | APNEA-ECG | MIMIC II |
|---|---|---|---|
| NAÏVE | 0.52/HR | 0.41/HR | 0.17/HR |
| BAYES NETWORK | 0.49/HR | 0.39/HR | 0.11/HR |
| LOGISTIC REGRESSION | 0.91/HR | 0.33/HR | 0.04/HR |
| C4.5 | 0.33/HR | 0.29/HR | 0.05/HR |
| SVM | 0.37/HR | 0.27/HR | 0.13/HR |
| VFI | 0.45/HR | 0.38/HR | 0.20/HR |
| ANN | 0.51/HR | 0.44/HR | 0.06/HR |

*Fig. 7.*

METHODS AND SYSTEMS FOR CALCULATING AND USING STATISTICAL MODELS TO PREDICT MEDICAL EVENTS

CROSS-REFERENCE(S) TO RELATED APPLICATION(S)

This application is a National Stage Entry of PCT/US2013/057137, filed Aug. 28, 2013, which claims the benefit of U.S. Provisional Application No. 61/694,171, filed Aug. 28, 2012, the entire disclosure of which is hereby incorporated herein by reference for all purposes.

STATEMENT OF GOVERNMENT LICENSE RIGHTS

This invention was made with Government support under LM007356, awarded by the National Institutes of Health. The Government has certain rights in the invention.

BACKGROUND

Recent advancements in sensor and wireless communication technologies have opened up many opportunities to acquire biomedical signals at a very low cost. Many sensors are compact enough to be worn by the subjects, and can continuously gather data for a prolonged period. These technologies have quickly found their natural applications in health care in the form of eHealth and telemedical systems.

Most of the early eHealth systems focus on remote monitoring and abnormality detection. While providing a low-cost and convenient way for health care personnel to monitor the well-being of patients, the majority of these systems are essentially infrastructures for data collection and storage. One of the main goals of the next generation of eHealth systems is to mine and analyze the sensor data for so-called "precursor patterns." These patterns are highly correlated to an ensuing medical condition or clinical episode. Using precursor patterns to predict medical events will be important for the next generation of eHealth systems.

Thus far, there have been several studies dedicated to identifying precursor patterns with a varying degree of success. However, one common problem with these studies is the requirement of domain-specific knowledge to develop their discovery algorithms. Also, most of the algorithms require prior knowledge of the duration of the precursor patterns, as well as the time the patterns are likely to occur relative to the clinical episode. Consequently, it is often impossible to apply a given precursor pattern discovery algorithm to a different medical condition without significant modification or degradation in performance.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method of generating a precursor pattern detection model for detecting an occurrence of a given type of medical event is provided. A computing device obtains annotated monitoring data, wherein the annotated monitoring data represents measurements of physical conditions of at least one patient. A computing device extracts a set of positive segments and a set of negative segments from the annotated monitoring data, wherein each positive segment is associated with an occurrence of a medical event of the given type, and wherein each negative segment is not associated with an occurrence of the medical event of the given type. A computing device executes a time filter on the set of positive segments to generate a set of filtered positive segments. A computing device executes a time filter on the set of negative segments to generate a set of filtered negative segments. A computing device extracts a set of extracted positive features from the set of filtered positive segments and a set of extracted negative features from the set of filtered negative segments. A computing device selects a set of selected positive features from the set of extracted positive features and a set of selected negative features from the set of extracted negative features.

A computing device calculates a precursor pattern detection model based on the set of selected positive features and the set of selected negative features, and a computing device stores, on a nontransitory computer-readable medium, the precursor pattern detection model. In some embodiments, a nontransitory computer-readable medium having computer-executable instructions stored thereon is provided wherein the instructions, in response to execution by one or more processors of one or more computing devices, cause the one or more computing devices to perform such a method. In some embodiments, a system comprising one or more computing devices configured to perform such a method is provided.

In some embodiments, a method of detecting an occurrence of a given type of medical event is provided. A precursor pattern detection model is retrieved from a precursor pattern data store. One or more monitoring devices are used to collect data from a patient. The collected data is analyzed using the precursor pattern detection model. In response to the analysis indicating that a precursor pattern has been detected in the collected data, an alert is caused to be presented to a caregiver. In some embodiments, a computing device configured to perform such a method is provided.

In some embodiments, a nontransitory computer-readable medium having computer-executable instructions stored thereon is provided, wherein the instructions, in response to execution by one or more processors of a computing device, cause the computing device to perform such a method.

DESCRIPTION OF THE DRAWINGS

The foregoing aspects and many of the attendant advantages of embodiments of the subject matter disclosed herein will become more readily appreciated as the same become better understood by reference to the following detailed description, when taken in conjunction with the accompanying drawings, wherein:

FIG. 5 is a table that illustrates various examples of classifiers used in various embodiments of the present disclosure;

FIG. 6 is a chart that illustrates prediction accuracy obtained for three datasets tested using an embodiment of the present disclosure:

FIG. 7 is a chart that illustrates false-positive rates of the three datasets tested using the embodiment of the present disclosure;

DETAILED DESCRIPTION

The present disclosure describes systems and methods for generalized precursor pattern discovery that work with a wide range of biomedical signals and applications. In some embodiments, the methods and systems do not require domain-specific knowledge or significant reconfiguration based on the medical event being analyzed, hence it is also possible to discover patterns previously unknown to experts.

System Overview

Figure 1:
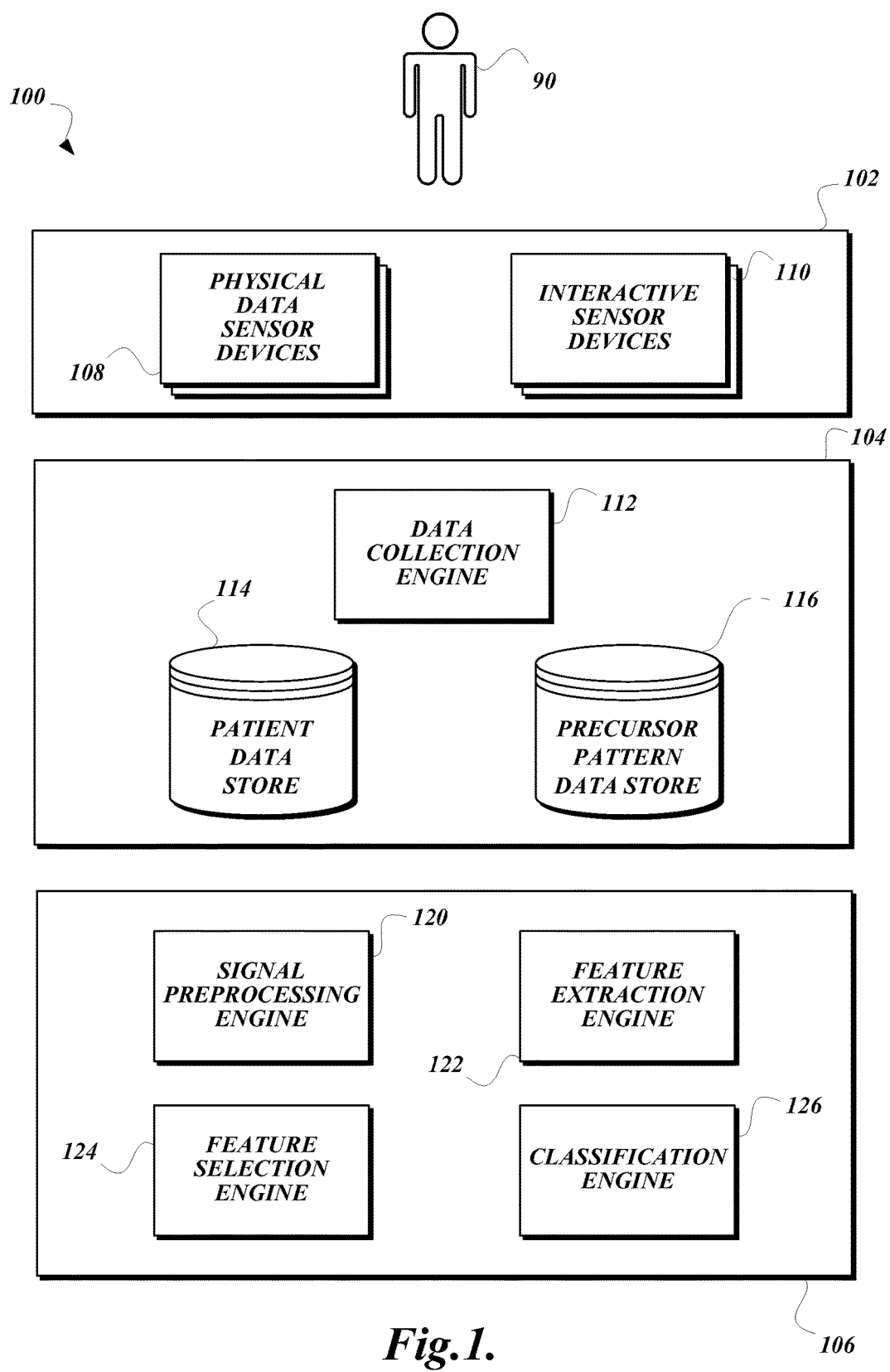
FIG. 1 is a block diagram that illustrates an exemplary embodiment of a precursor pattern analysis system according to various aspects of the present disclosure.

FIG. 1 is a block diagram that illustrates an exemplary embodiment of a precursor pattern analysis system 100 according to various aspects of the present disclosure. As illustrated, the precursor pattern analysis system 100 includes three tiers: a patient monitoring system 102, a patient data processing system 104, and a precursor pattern detection system 106. Each of the systems 102, 104, 106 may include one or more computing devices configured to provide the engines, data stores, and/or services illustrated and described herein as part of the respective system 102, 104, 106.

In some embodiments, the patient monitoring system 102 is configured to collect particular measurements form the patient 90, and to transmit the collected information to the patient data processing system 104 for processing and storage. The precursor pattern detection system 106 is configured to access the collected information stored by the patient data processing system 104, to process the collected information to detect one or more precursor patterns, and to provide precursor pattern detection models to the patient data processing system 104 for storage. In some embodiments, the patient monitoring system 102 may be further configured to use the precursor pattern detection models to monitor patients for occurrences of the precursor patterns.

In some embodiments, the patient monitoring system 102 may be located at the patient's home (or otherwise placed in a location easily accessible to the patient), while the patient data processing system 104 and the precursor pattern detection system 106 are placed in a central location such that multiple patient monitoring systems 102 in multiple locations may share the resources of a single patient data processing system 104 and/or precursor pattern detection system 106. In such embodiments, the components of the precursor pattern analysis system 100 may communicate with each other using any suitable communication technology, such as wired or wireless Internet communication, direct dial telephone or ISDN communication, and/or any other suitable communication technology. In some embodiments, the patient monitoring system 102, the patient data processing system 104, and/or the precursor pattern detection system 106 may be provided by a single computing device, or by multiple computing devices each located on the same network, thus obviating the need for long-distance communication between the elements of the precursor pattern analysis system 100. Though FIG. 1 illustrates various components as being included in either the patient monitoring system 102, the patient data processing system 104, or the precursor pattern detection system 106, in some embodiments, the illustrated components may be moved from one of the illustrated systems 102, 104, 106 to another of the illustrated systems 102, 104, 106 or split between two or more of the illustrated systems 102, 104, 106; two or more of the illustrated systems 102, 104, 106 may be combined into a single system; and/or one of the illustrated systems 102, 104, 106 may be broken into multiple separate systems.

As illustrated, the patient monitoring system 102 includes one or more physical data sensor devices 108 and one or more interactive sensor devices 118 for collecting measurements from a patient 90. The physical data sensor devices 108 are physical devices that may automatically perform a measurement of a physical value, and may cause the detected physical value to be automatically transmitted to the patient data processing system 104 without further interaction from the patient 90. For example, the physical data sensor devices 108 may include, but are not limited to, an electronic sphygmomanometer, an electronic thermometer, an electronic heart rate monitor, a pedometer, an electronic scale, an electroencephalograph machine, an electrocardiogram machine, a motion sensor, and/or the like. The interactive sensor devices 110 are physical devices that collect information entered by the patient 90 (or by a caregiver operating the patient monitoring system 102 on behalf of the patient 90). In some embodiments, an interactive sensor device 110 may be configured to present a prompt to the patient 90 to instruct the patient 90 to perform a measurement with a non-connected medical device or answer a survey question, and may subsequently allow the patient 90 to enter the result of the measurement or the answer the survey question. The interactive sensor device 110 then sends the collected information to the patient data processing system 104. In some embodiments, the interactive sensor devices 110 may include a desktop computing device executing a stand-alone application or presenting a web site, a mobile computing device such as a smart phone, a tablet computing device, a custom computing device configured to present an interface to the patient monitoring system 102, and/or the like.

As illustrated, the patient data processing system 104 includes a data collection engine 112. In general, the word "engine" (used interchangeably with the word application or module), as used herein, refers to logic embodied in hardware or software instructions, which may be written in a programming language, such as C, C++, COBOL, JAVA™, PHP, Perl, HTML, CSS, JavaScript, VBScript, ASPX, Microsoft .NET™, and/or the like. An engine may be compiled into executable programs or written in interpreted programming languages. Software engines or applications may be callable from other engines or from themselves. Generally, the engines or applications described herein refer to logical modules that can be merged with other engines or applications, or can be divided into sub-engines. The engines or applications may be stored in any type of computer-readable medium or computer storage device and be stored on and executed by one or more general purpose computers, thus creating a special purpose computer configured to provide the engine or application.

In some embodiments, the data collection engine 112 may provide a web service or other appropriate application programming interface (API) with which the patient monitoring system 102 communicates, such that collected data may be received by the data collection engine 112 via the API. In some embodiments, the data collection engine 112 may generate a web-based interface to be presented to the patient 90 by the patient monitoring system 102 and into which the collected data may be directly entered. In some embodiments, the data collection engine 112 may cause the raw collected data to be stored, while in some embodiments, the data collection engine 112 may perform filtering or other data cleaning tasks before causing the collected data to be stored. Further functionality of the data collection engine 112 is described below.

The illustrated patient data processing system 104 also includes a patient data store 114, and a precursor pattern data store 116. As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed packet switched network. However, any other suitable storage technique and/or device capable of quickly and reliably providing the stored data in response to queries may be used, and the computing device may be accessible locally instead of over a network, or may be accessible over some other type of suitable network or provided as a cloud-based service. A data store may also include data stored in an organized manner on a storage medium 1108, as described further below. One of ordinary skill in the art will recognize that separate data stores described herein may be combined into a single data store, and/or a single data store described herein may be separated into multiple data stores, without departing from the scope of the present disclosure.

In some embodiments, the patient data store 114 is configured to store the data collected from the patient 90 by the patient monitoring system 102. In some embodiments, the patient data store 114 may also be configured to store other information related to patients, such as demographic information, associated health care provider information, login and password information, and/or the like. In some embodiments, the patient data store 114 may be configured to store data collected from the patient 90 as well as data that has been processed by the precursor pattern detection system 106. In some embodiments, the precursor pattern data store 116 is configured to store precursor pattern detection models generated by the precursor pattern detection system 106 based on the collected patient data. The precursor pattern detection models stored in the precursor pattern data store 116 may be retrieved by the patient monitoring system 102 in order to monitor for occurrences of the precursor patterns in new data collected from the patient 90. In some embodiments, the precursor pattern data store 116 may also store other information associated with the precursor pattern detection models, such as information about associated medical conditions, instructions to be executed upon detection of a given precursor pattern, and/or the like. Further aspects of the patient data store 114 and the precursor pattern data store 116 are discussed below.

As illustrated, the precursor pattern detection system 106 includes a signal preprocessing engine 120, a feature extraction engine 122, a feature selection engine 124, and a classification engine 126. In some embodiments, the signal preprocessing engine 120 is configured to preprocess collected data to place it in a format suitable for further processing by the other components of the precursor pattern detection system 106. The preprocessing may include identifying and/or removing out-of-range, missing, or otherwise invalid data; normalizing collected data received from different patient monitoring systems 102 or sensor devices to have matching scales and/or frequencies; and/or the like. In some embodiments, the preprocessing engine is configured to extract positive segments and negative segments from the collected data, wherein the positive segments are associated with medical events to be predicted, and the negative segments are not associated with medical events to be predicted. In some embodiments, the preprocessing engine is also configured to apply time filters to the extracted segments, such that the segments are filtered down to their most relevant portions with respect to significance in detecting the precursor pattern. Further operations of the signal preprocessing engine 120 are discussed below.

In some embodiments, the feature extraction engine 122 is configured to extract features from the segments extracted by the signal preprocessing engine 120. As discussed in further detail below, the features are a simplified representation of some aspect of the data of the segment, such as a mathematical property (standard deviation, mean, and/or the like), a transformation (a wavelet transform and/or the like), and/or any other simplified representation of the data. In some embodiments, the feature selection engine 124 is configured to select a set of relevant features extracted by the feature extraction engine 122. In some embodiments, the classification engine 126 is configured to execute a classification algorithm over the features selected by the feature selection engine 124, and to thereby generate the precursor pattern detection model. Further details of the functionality of each of these engines are provided below.

Detecting Precursor Patterns

Figure 2A:
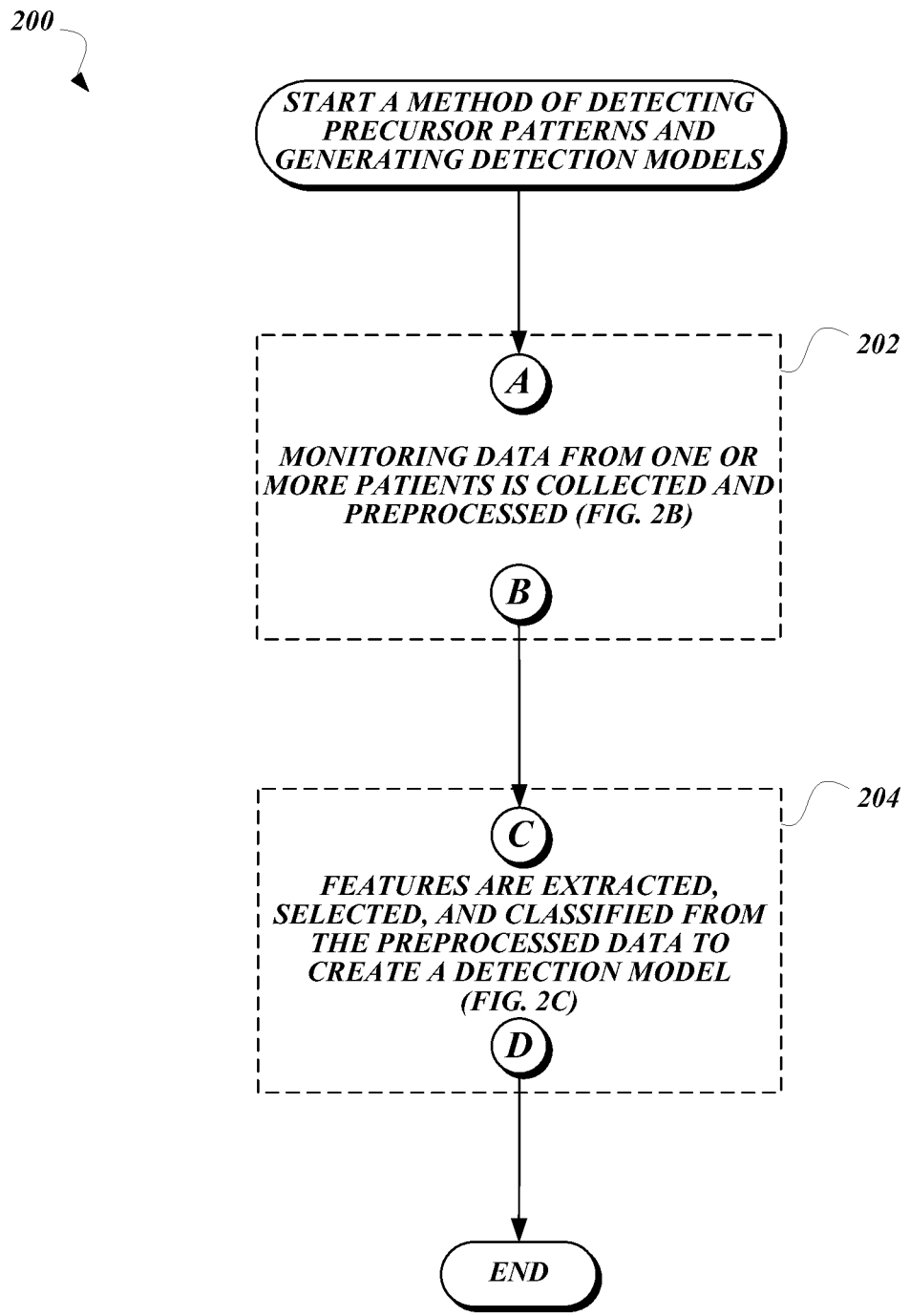
FIGS. 2A-2C are a flowchart that illustrates an exemplary embodiment of a method of detecting precursor patterns and generating detection models according to various aspects of the present disclosure.
Figure 2B:
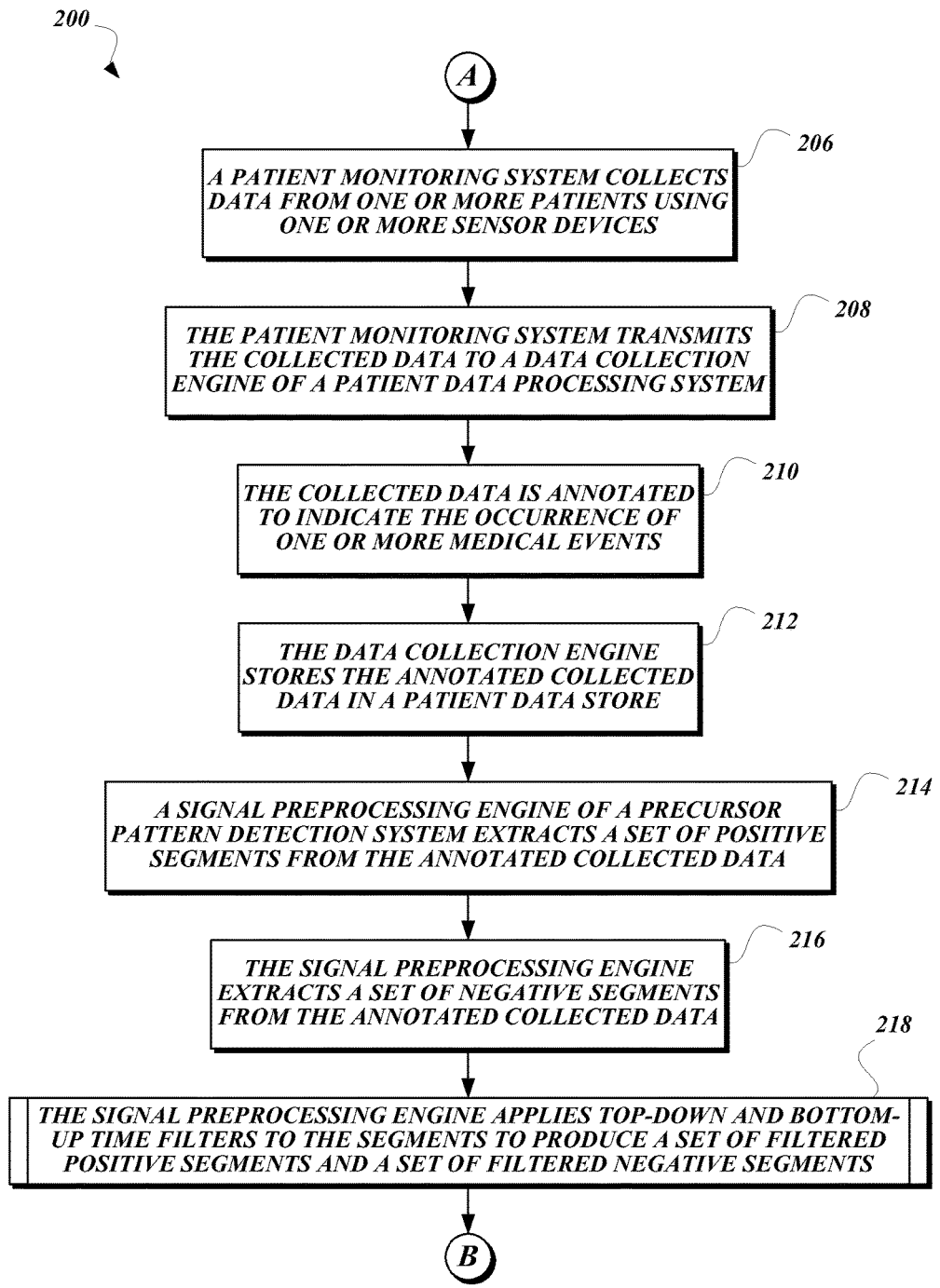
Figure 2C:
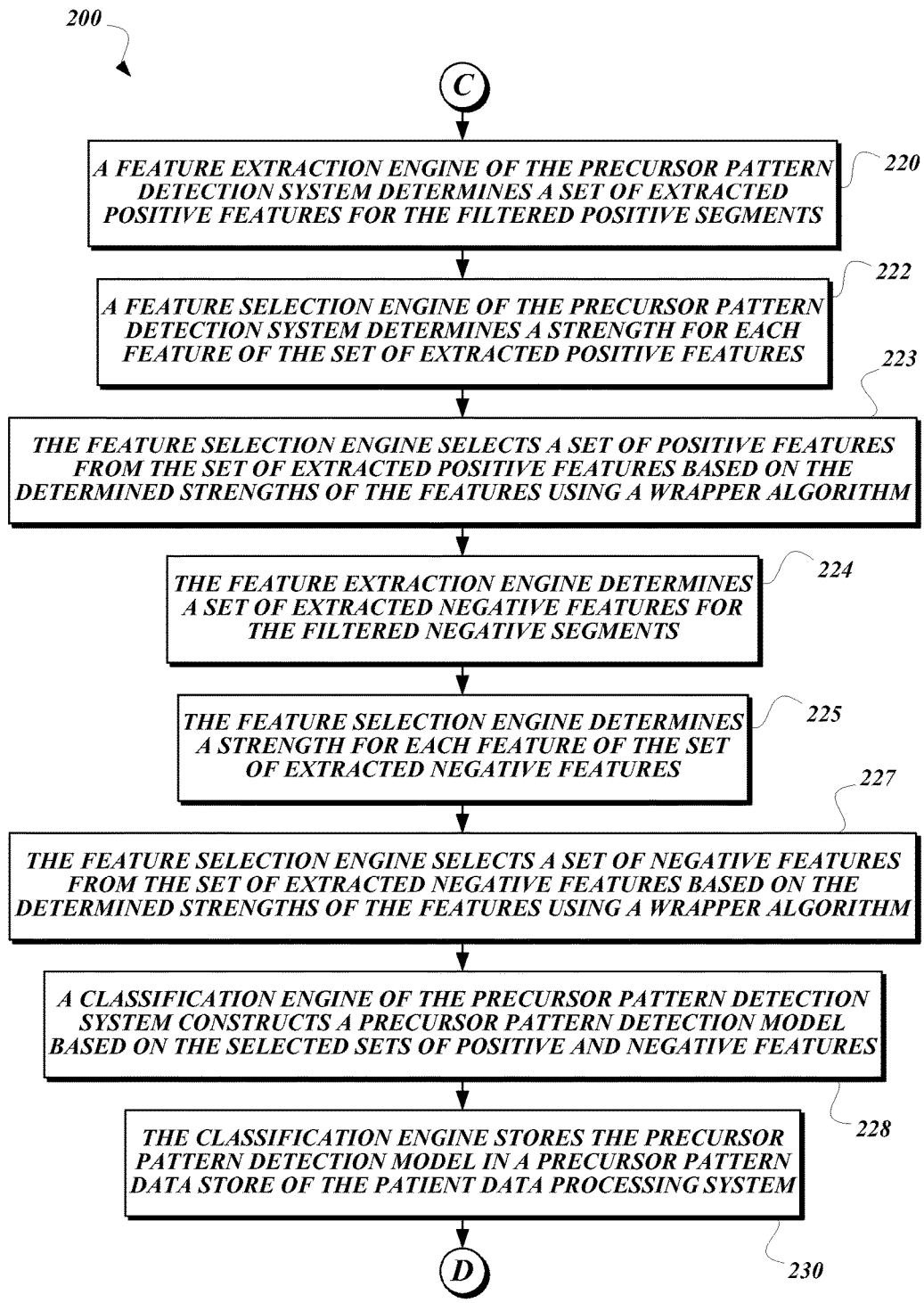

FIGS. 2A-2C are a flowchart that illustrates an exemplary embodiment of a method of detecting precursor patterns and generating detection models according to various aspects of the present disclosure. From a start block, the method 200 proceeds to a set of method steps 202 defined between a start terminal ("terminal A") and an exit terminal ("terminal B"), wherein monitoring data from one or more patients is collected and preprocessed.

From terminal A (FIG. 2B), the method 200 proceeds to block 206, where a patient monitoring system 102 collects data from one or more patients 90 using one or more sensor devices. The one or more sensor devices may include one or more physical data sensor devices 108, such as sphygmomanometers, electroencephalograph machines, electrocardiogram machines, thermometers, scales, and/or the like; one or more interactive sensor devices 110, such as a computing device configured to collect survey responses from the patient 90, a mobile device configured to collect information input by the patient 90, and/or the like; and/or any other suitable sensor device. Next, at block 208, the patient monitoring system 102 transmits the collected data to a data collection engine 112 of a patient data processing system 104. As described above, the collected data may be transmitted to the patient data processing system 104 via the internet, a modem, a leased line, or via any other suitable communication technology. As also described above, in some embodiments the data collection engine 112 may provide a web service or other suitable API to receive the data from the patient monitoring system 102.

At block 210, the collected data is annotated to indicate the occurrence of one or more medical events. In some embodiments, this annotation may occur automatically by the data collection engine 112 or the sensor devices themselves. For example, in some embodiments, an annotation may be made automatically in the collected data by an ICU monitor upon detecting that a vital sign being tracked by the ICU monitor has crossed a predetermined threshold. In some embodiments, this annotation may be added manually by an expert reviewing the collected data. For example, if a patient 90 is being monitored for sleep apnea and the collected data includes a polysomnogram, a reviewing physician may read the polysomnogram and manually annotate the record to indicate the sleep apnea events. At block 212, the data collection engine 112 stores the annotated collected data in a patient data store 114.

In some embodiments, the actions illustrated in blocks 206-212 and described above may be performed multiple times to gather a set of data to be analyzed for task optimization. The repetition of the actions in blocks 206-212 may be performed with a single patient over a period of time, or may be performed using data from many patients to provide greater statistical rigor for the conclusions drawn. In some embodiments, the data to be analyzed by the remainder of the method 200 may be collected using techniques other than those described above.

At block 214, a signal preprocessing engine 120 of a precursor pattern detection system 106 extracts a set of positive segments from the annotated collected data stored in the patient data store 114, and at block 216, the signal preprocessing engine 120 extracts a set of negative segments from the annotated collected data. The positive segments are segments of the annotated collected data associated with instances of the medical event during which precursor patterns are believed to occur. The negative segments are segments of the annotated collected data which are not associated with instances of the medical event and so are not expected to include the precursor patterns. In some embodiments, the positive segments may be extracted by taking a segment of a predetermined length before an annotated medical event. The negative segments may likewise be extracted by taking a segment of the same predetermined length from a portion of the annotated collected data that is distant from any annotated medical event, or from a portion of the annotated collected data associated with a patient that did not exhibit the medical event.

Figure 3A:
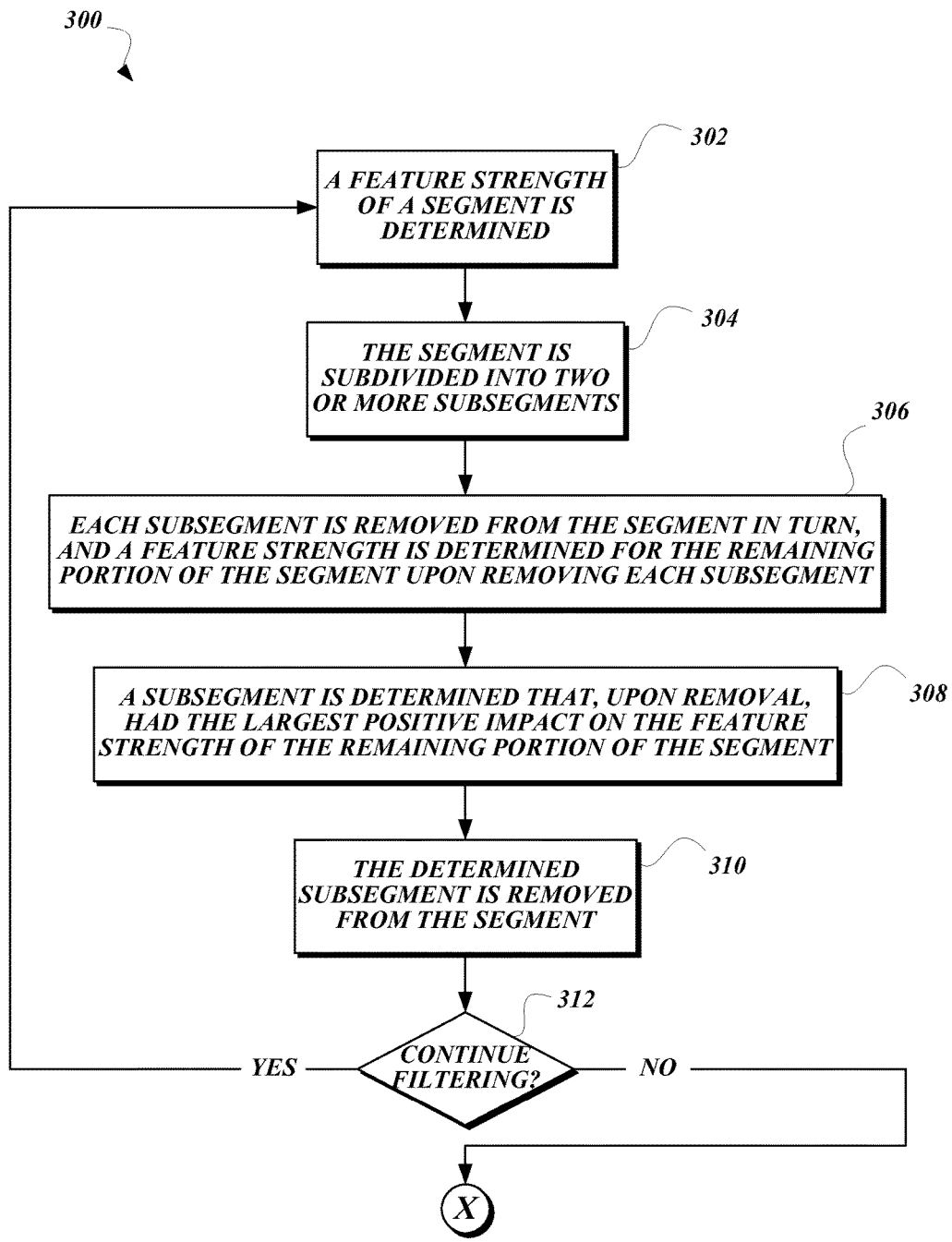
FIGS. 3A-3B are a flowchart that illustrates an exemplary embodiment of a top-down and bottom-up time filter procedure according to various aspects of the present disclosure.
Figure 3B:
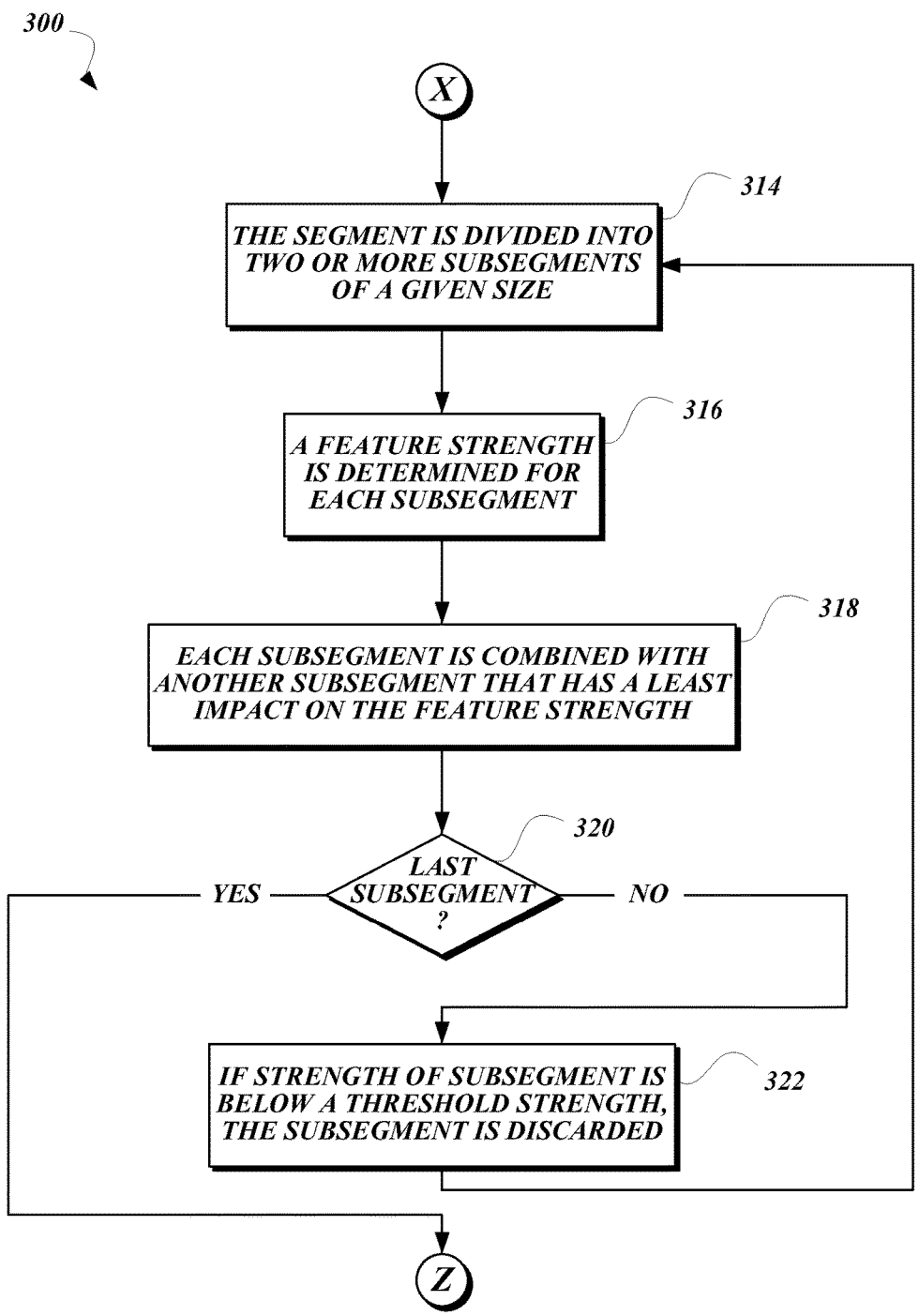

The method 200 then proceeds to procedure block 218, where the signal preprocessing engine 120 applies top-down and bottom-up time filters to the segments to produce a set of filtered positive segments and a set of filtered negative segments. The time filters help remove portions of the segments that do not significantly contribute to the distinctiveness of the segments, thereby increasing the strength of the detection functionality while also reducing the amount of data to be processed. An example top-down and bottom-up time filter procedure is illustrated in FIGS. 3A-3B, and is discussed further below. The method 200 then proceeds to terminal B.

From terminal B (FIG. 2A), the method 200 proceeds to a set of method steps 204 defined between a start terminal ("terminal C") and an exit terminal ("terminal D"), wherein features are extracted, selected, and classified from the preprocessed data to create a detection model. From terminal C (FIG. 2C), the method 200 proceeds to block 220, where a feature extraction engine 122 of the precursor pattern detection system 106 determines a set of extracted positive features for the filtered positive segments Each feature is a high-level, succinct way of representing or summarizing the original data in a simplified form. For example, in some embodiments, a feature may be extracted by computing a standard deviation of data points within the segment, thus representing an aspect of multiple data points with a single value. As another example, a feature for a segment may be extracted by determining a delta of values within the segment compared to values within a previous segment.

As yet another example, features could be extracted that encompass both spectral and temporal information of the signal. The spectral information is generic and widely applicable to many types of signals and many types of medical events, while the temporal information can help identify the time and length of the precursor pattern. In some embodiments, such features that encompass both spectral and temporal information of the signal may be extracted by performing a wavelet transform, where the signal is represented using orthonormal function basis called a mother wavelet. A Haar wavelet transform (or Daubenchies-2) may be particularly suitable for extracting features, as it has a low O(n) complexity and has been shown to work well with time series data. The wavelet coefficients may be computed at multiple resolutions, each at half of the scale of the previous one. These coefficients are then used as the extracted features.

In some embodiments, multiple features may be extracted for a single segment, such as a mean and a standard deviation, a standard deviation and a delta, a standard deviation and a wavelet transform, or any other combination of two or more features. Likewise, multiple features may be extracted for a single segment based on multiple signals included in the segment. For example, feature extraction may extract a standard deviation of an electrocardiogram signal, and may extract a delta for a body weight signal, both for the same segment.

Next, at block 222, a feature selection engine 124 of the precursor pattern detection system 106 determines a strength for each feature of the set of extracted positive features, and at block 223, the feature selection engine 124 selects a set of features from the set of extracted positive features based on the determined strengths of the features using a wrapper algorithm. Performing feature selection helps reduce the amount of data to be processed to make classification more efficient and accurate. For example, a one minute segment on a 128 Hz signal generates a total of 7680 coefficients when performing a Haar wavelet transform. Building a classification model using every available coefficient would not only be slow, but would also be likely to result in overfitting. Only a small portion of the coefficients are likely correlate to the medical event and thus constitute the precursor pattern.

Generally, there are three types of feature selection algorithms: Wrapper, Embedded, and Hybrid. Wrapper algorithms may be the most appropriate, as they select features based on aspects of the features, such as correlation, relevance, and redundancy, and are therefore model-agnostic. In some embodiments, Information Gain may be used to calculate the feature strength and form the basis for feature selection. The Information Gain (IG) for a feature, given a set of training samples $S_X$ is:

$$IG(S_X, f_i) = H(S_X) - (S_X | f_i)$$

H(S) is the information entropy of S:

$$H(S) = -\sum_{i=1}^{n} p(S_i)\log p(S_i)$$

The conditional entropy $H(S_X|f_i)$ is therefore:

$$H(S_X \mid f_i) = \sum_{x \in S_X} p(x, f_i)\log \frac{p(f_i)}{p(x, f_i)}$$

In other words, $IG(S_X, f_i)$ is the change in entropy if $f_i$ is known in advance. A feature with small IG is considered less relevant and can be discarded without weakening the classification model. In some embodiments, features having a strength below a predetermined threshold may be discarded. In some embodiments, a top percentage or absolute number (e.g., top-100) of features as ranked by strength may be retained, and the rest of the features may be discarded.

At block 224, the feature extraction engine 122 determines a set of extracted negative features for the filtered negative segments; at block 225, the feature selection engine 124 determines a strength for each feature of the set of extracted negative features; and at block 227, the feature selection engine 124 selects a set of negative features from the set of extracted negative features based on the determined strengths of the features using a wrapper algorithm. In blocks 224, 225, and 227, the method 200 performs actions similar to those discussed above with respect to blocks 220, 222, and 223, respectively, but over the filtered negative segments as opposed to the filtered positive segments. Because these actions are similar to those discussed above with respect to blocks 220, 222, and 223, the actions performed at blocks 224, 225, and 227 are not described further for the sake of brevity.

The method 200 then proceeds to block 228, where a classification engine 126 of the precursor pattern detection system 106 constructs a precursor pattern detection model based on the selected set of features. While constructing the model, it is important to separate the training data from the testing data to prevent model overfitting and overly optimistic results. However, if the number of positive segments is limited due to the rare nature of the medical event within the collected data, it is also possible to perform n-fold validation using the same number of positive and negative segments. The method 200 is classifier agnostic, and so any type of classifier known to one of skill in the art may be used to construct the precursor pattern detection model from the selected set of features. Some examples of suitable classifier algorithms include, but are not limited to, Naïve Bayes, Bayes Network, Logistic Regression, C4.5 Decision Tree, Support Vector Machine (SVM), Voting Feature Interval (VFI), Artificial Neural Network (ANN), Nearest Neighbor (kNN), and Ripple-Down Rule Learner (RIDOR). Though the use of these classifier algorithms are known to one or skill in the art, brief descriptions of some of these classifier algorithms have nevertheless been included in FIG. 5.

After the precursor pattern detection model is constructed, the method 200 proceeds to block 230, where the classification engine 126 stores the precursor pattern detection model in a precursor pattern data store 116 of the patient data processing system 104. Information stored in the precursor pattern data store 116 along with the precursor pattern detection model may include an identification of the medical event to be detected by the precursor pattern detection model, an identification of the signals considered by the precursor pattern detection model, a set of instructions to be executed upon detecting the precursor pattern, and/or the like. The method 200 then proceeds to terminal D, and from terminal D (FIG. 2A) to an end block, where the method 200 terminates.

FIGS. 3A-3B are a flowchart that illustrates an exemplary embodiment of a top-down and bottom-up time filter procedure according to various aspects of the present disclosure. The illustrated procedure 300 is an example of a procedure suitable for execution at block 218 in the method 200 described above. In some embodiments, all segments of the annotated collected data are lined up and considered together. For example, if segments are five days long, all of the first days of the segment are considered together, all of the second days of the segment are considered together, and so on, such that a determination can be made regarding the strength of portions of a generic segment as opposed to an individual actual segment.

The procedure 300 begins at block 302, where a feature strength of a segment is determined. Feature strength may be determined using any suitable technique for determining a correlation between the feature and the classification of the segment. For example, in some embodiments, an Information Gain (IG) value is computed and used as the feature strength. The procedure 300 then proceeds to block 304, where the segment is subdivided into two or more subsegments. In some embodiments, the segment may be subdivided based on data granularity. For example, if there is one data point per day, a multi-day segment may be subdivided into days. In some embodiments, the subdivisions may include multiple data points if data granularity is high compared to segment length. For example, if data is sampled at 60 Hz and the segment is a minute long, the segment may be subdivided into 60-data-point subdivisions (one subdivision per second).

At block 306, each subsegment is removed from the segment in turn, and a feature strength is determined for the remaining portion of the segment upon removing each subsegment. Next, at block 308, a subsegment is determined that, upon removal, had the largest positive impact on the feature strength of the remaining portion of the segment, and at block 310, the determined subsegment is removed from the segment. For example, if the segment is five days long and has been subdivided into five single-day subdivisions, removing day 1 may have no impact on the feature strength of the subsegment consisting of days 2, 3, 4, and 5 compared to the feature strength of the segment as a whole. Meanwhile, removing day 3 may increase the feature strength of the subsegment consisting of days 1, 2, 4, and 5 compared to the feature strength of the segment as a whole. Accordingly, in this example day 3 would be removed, and the remaining segment would consist of days 1, 2, 4, and 5. The intuition is that portions of the segment that do not significantly contribute to the feature strength can be removed to both streamline processing and to increase the predictive strength of the remaining portions of the segment.

In some embodiments, division into subsegments may include separating individual signals or features. For example, in the five-day example segment described above, there may be two features computed for the segment. The two features may be extracted from the same signal (e.g., a standard deviation and a mean of a time series), or could be extracted from different signals (e.g., a standard deviation of a time series of a first EEG signal, and a standard deviation of a time series of a second EEG signal). In such embodiments, each extracted feature may be divided into a separate subsegment, such that when the five-day example segment is broken into day-long subsegments, ten subsegments may be created (one for each of the two features for each day).

Once the determined subsegment is removed from the segment, the procedure 300 proceeds to a decision block 312, where a determination is made as to whether top-down filtering should continue on the segment. In some embodiments, top-down filtering is continued if the strength of the segment is not yet above a predetermined threshold strength. In some embodiments, top-down filtering is continued even if the strength of the segment is above a predetermined threshold strength, as long as the strength of the segment is still increasing as a result of the execution of the filter. If the result of the determination at decision block 312 is YES, the procedure 300 returns to block 302, and another iteration of the top-down filtering steps is performed on the segment to remove another subsegment. Otherwise, if the result of the determination at decision block 312 is NO, the procedure 300 advances to a continuation terminal ("terminal X").

From terminal X (FIG. 3B), the procedure 300 proceeds to block 314, where the segment is divided into two or more subsegments of a given size. The size of the subsegments may be determined similarly to the subsegments discussed above, and the subsegments at block 314 may be the same size as the subsegments in the top-down filtering discussed above, or may be a different size. At block 316, a feature strength is determined for each subsegment. Next, at block 318, each subsegment is combined with another subsegment that has a least negative impact on the feature strength. This bottom-up combination of subsegments further reduces the number of features present without negatively impacting the overall predictive strength of the segment.

The procedure 300 proceeds to a decision block 320, where a determination is made as to whether the current subsegment is the last remaining subsegment. If the result of the determination at decision block 320 is YES, the procedure 300 advances to a continuation terminal ("terminal Z"). Otherwise, if the result of the determination at decision block 320 is NO, the procedure 300 advances to block 322, where, if a strength of the subsegment is below a threshold strength, the subsegment is discarded, otherwise, the subsegment is retained as part of the segment. The procedure 300 then returns to block 314 to repeat the bottom-down filtering steps.

From terminal Z, the procedure 300 may exit to return to an overarching method (such as method 200 described above), or the procedure 300 may return to block 302 to further filter the filtered segments by iterating over the procedure 300 again. This iteration may continue until the procedure 300 does not change the filtered segment.

Utilizing Precursor Pattern Detection Models

Figure 4:
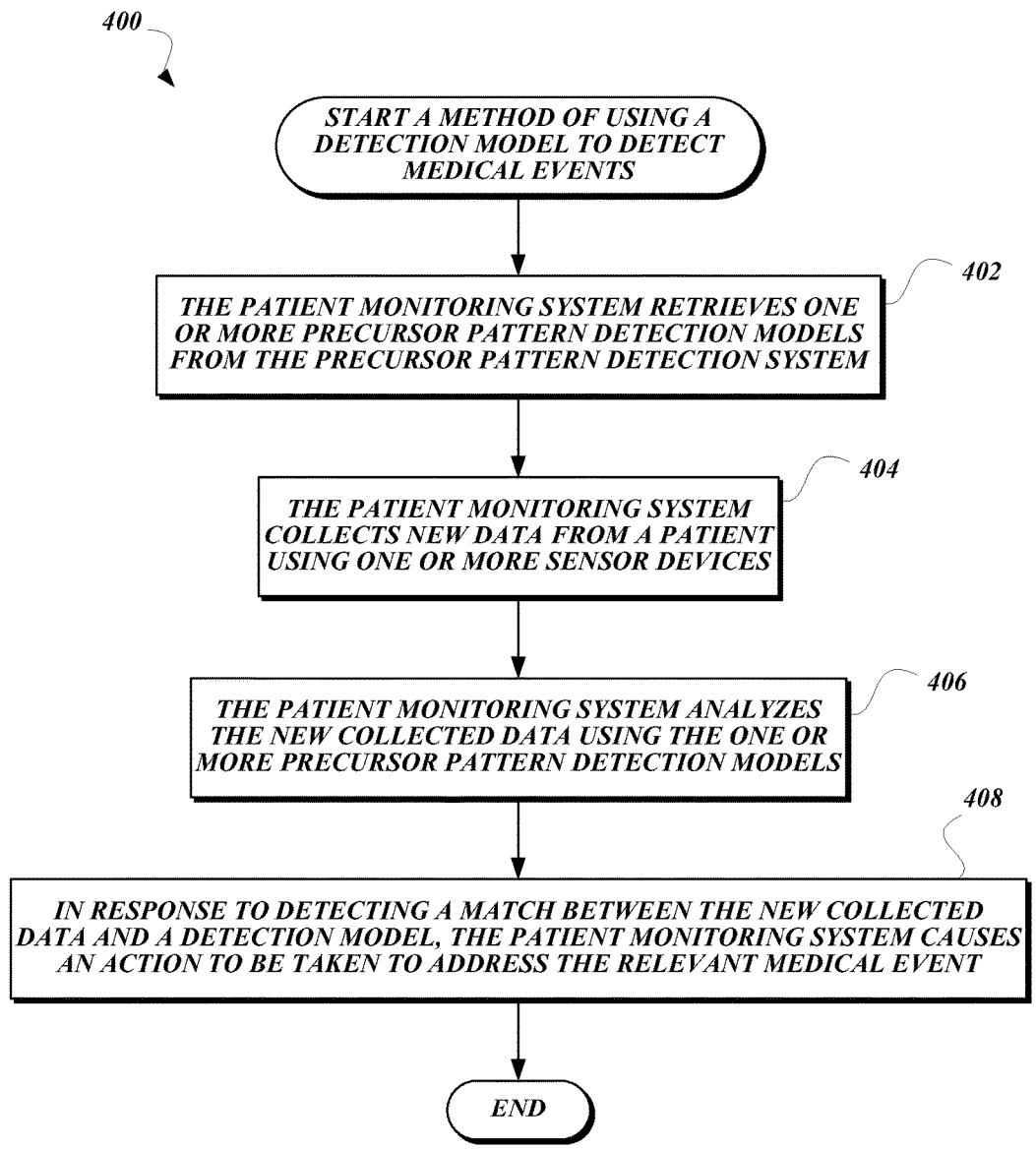
FIG. 4 is a flowchart that illustrates an exemplary embodiment of a method of using a precursor pattern detection model to detect medical events according to various aspects of the present disclosure.

Once a precursor pattern detection model has been created, that model can be used while monitoring a patient 90 to detect occurrences of the precursor pattern and cause the associated medical condition to be addressed. FIG. 4 is a flowchart that illustrates an exemplary embodiment of a method of using a precursor pattern detection model to detect medical events according to various aspects of the present disclosure. From a start block, the method 400 proceeds to block 402, where the patient monitoring system 102 retrieves one or more precursor pattern detection models from the precursor pattern detection system 104. In some embodiments, the patient monitoring system 102 may be configured to monitor the patient 90 for occurrences of a single medical event, while in other embodiments, the patient monitoring system 102 may be configured to gather as much information as is practical from the patient 90 and to search for precursor patterns indicating multiple medical events.

The method 400 proceeds to block 404, where the patient monitoring system 102 collects new data from a patient 90 using one or more sensor devices, including the physical data sensor devices 108 and the interactive sensor devices 110. In some embodiments, fewer sensor devices may be used than during the data collection process, as the precursor pattern detection models may indicate that only some of the collected data was relevant. In some embodiments, more sensor devices than are relevant to the precursor pattern detection models may be used.

At block 406, the patient monitoring system 102 analyzes the new collected data using the one or more precursor pattern detection models. At block 408, in response to detecting a match between the new collected data and a precursor pattern detection model, the patient monitoring system 102 causes an action to be taken to address the relevant medical event. In some embodiments, the action may include executing the instructions associated with the precursor pattern detection model in the precursor pattern data store 116. The instructions may cause a computing device to inform the patient that they should seek care; may cause a message to be sent to a care provider, may cause a medication to be automatically administered to the patient 90; may cause an amount of monitoring of the patient to be changed, or may cause any other suitable action to occur. As illustrated, the method 400 then proceeds to an end block and terminates, though in some embodiments, the method 400 may run continuously to collect data from patients, analyze the data using the precursor pattern detection models, and take action when appropriate, until the method 400 is terminated by the patient 90 or other user.

Test Results

Multiple tests were performed to verify that the above-described systems and methods can be used to generate precursor pattern detection models for multiple different types of medical events. For each different type of medical event, the above-described method was able to generate effective precursor pattern detection models.

For the first three tests, datasets from the publicly available PhysioNet database (described in Goldberger et al., "Physiobank, physiotoolkit, and physionet: Components of a new research resource for complex physiologic signals," *Circulalion*, Volume 101, No. 23, pp. e215-e220 (2000)) were used to build precursor pattern detection models for three different medical events: epileptic seizures, apnea, and vital sign alerts.

The chbmit dataset from PhysioNet was used to build the precursor pattern detection model for epileptic seizures. This dataset was collected at the Children's Hospital Boston. It consists of EEG recordings of 22 pediatric subjects with epileptic seizure. The EEG signals are sampled at 256 Hz with 16-bit resolution. During the 800 hours of recordings, there are 129 instances of annotated seizure attacks.

The apnea-ecg dataset from PhysioNet was used to build the precursor pattern detection model for apnea. This dataset comprises 70 records of a continuous electrocardiography (ECG) signal, sampled at 100 Hz with 16-bit resolution, and a set of apnea annotation derived by human experts at 1-minute intervals. The total recording lasts about 500 hours.

The MIMIC II dataset was used to build the precursor pattern detection model for vital sign alerts. The dataset is made up of 4448 records from ICU patients. The records include ECG, blood pressure, respiration, and vital signs. The alerts are annotated automatically by an ICU monitor.

For each of these datasets, the method 200 discussed above was performed to identify the precursor patterns, and seven well-known classifiers were used to generate the precursor pattern detection models and to validate their performance. The classifiers used were Naïve Bayes, Bayes Network, Logistic Regression, C4.5 Decision Tree, Support Vector Machine (SVM), Voting Feature Interval (VFI), and Artificial Neural Network (ANN). Though use of each of these classifiers is well known to one of ordinary skill in the art, brief descriptions of some these classifiers are available in FIG. 5.

The first metric used to evaluate the performance of the generated precursor pattern detection models was prediction accuracy. Given the limited number of positive segments in the datasets, the experiments were conducted using 10-fold validation. A 10-minute prediction horizon (the initial length of the positive and negative segments) was used for each experiment and the same number of positive and negative segments were used in each case to prevent screwing.

FIG. 6 is a chart that illustrates the prediction accuracy obtained for these three datasets for each classifier. From these results, it is clear that the prediction accuracy is fairly consistent for all three datasets regardless of the type of classifier used. The highest accuracy of 84.7% is achieved using SVM based on the precursor pattern detection model built for apnea-ecg. Overall, C4.5, SVM, and ANN perform slightly better than other classifiers in terms of prediction accuracy. Note that while the results here are comparable to some reported in other studies, the method and system described above do not require any medical domain expertise or analysis to attain this level of accuracy.

The second part of the experiments investigate the false-positive rate, measured in the number of false-positive indications per hour. To measure false-positive rate, the precursor patterns detection models are used to classify all unseen negative segments in the dataset. Ideally, none of these segments should trigger a positive prediction, thus resulting in a zero false-positive rate.

FIG. 7 is a chart that illustrates the false-positive rate of all three datasets using each different type of classifier. The chbmit and apnea-ecg datasets produce similar false-positive rates ranging from 0.29/hr to 0.91/hr, which is considerably higher than that of MIMIC II. One possible explanation for the difference is misalignment. The annotations in chbmit and apnea-ecg are done manually, while the MIMIC II dataset contains automatic annotations generated by machines. The false-positive rate should be reduced if the annotations are more precisely aligned with the medical events being annotated. In terms of differences between classifiers, C4.5 once again produces the best overall results, followed closely by SVM and ANN. While Logistic Regression achieves the lowest false-positive rate of 0.04/hr for MIMIC II, it performs poorly for chbmit. This inconsistency suggests that Logistic Regression may not be a suitable classifier for the generalized method.

The tests also showed the ability of the method to discover non-trivial patterns that are not known to experts. For example, when selecting the most prominent features in the chbmit dataset, it was discovered that the top-100 features consist entirely of signals acquired from only two EEG channels: $F_4$-$C_4$ and $F_{p1}$-$F_3$. In other words, the method was able to determine that these are the only two channels that are relevant for seizure prediction. Likewise, the temporal-spectral distribution of the top-100 most relevant features for the MIMIC II dataset indicated that the majority of the most relevant features were concentrated with frequency less than 50 Hz and within 5 minutes prior to the alerts. This suggests that a reliable prediction can still be made even if the signals were sampled at a lower sampling frequency and a shorter prediction horizon.

A fourth study was performed to create a precursor pattern detection model for predicting the worsening of heart failure symptoms. Previously, the most widely used metric to predict the worsening of heart failure symptoms was daily weight change (DWC). It is even recommended by the American College of Cardiology/American Health Association as a potential indicator for water retention, which leads to swollen ankles and other heart failure symptoms. However, several studies have shown that DWC has relatively weak correlation with the worsening of heart failure symptoms. Clinical trials of remote patient monitoring symptoms have also anecdotally shown this poor predictive power: when medical staff followed up with patients upon observing a DWC of more than two pounds, the patient almost always attributed the change to food or normal weight fluctuation, and denied any worsening of heart failure symptoms.

Figure 8A:
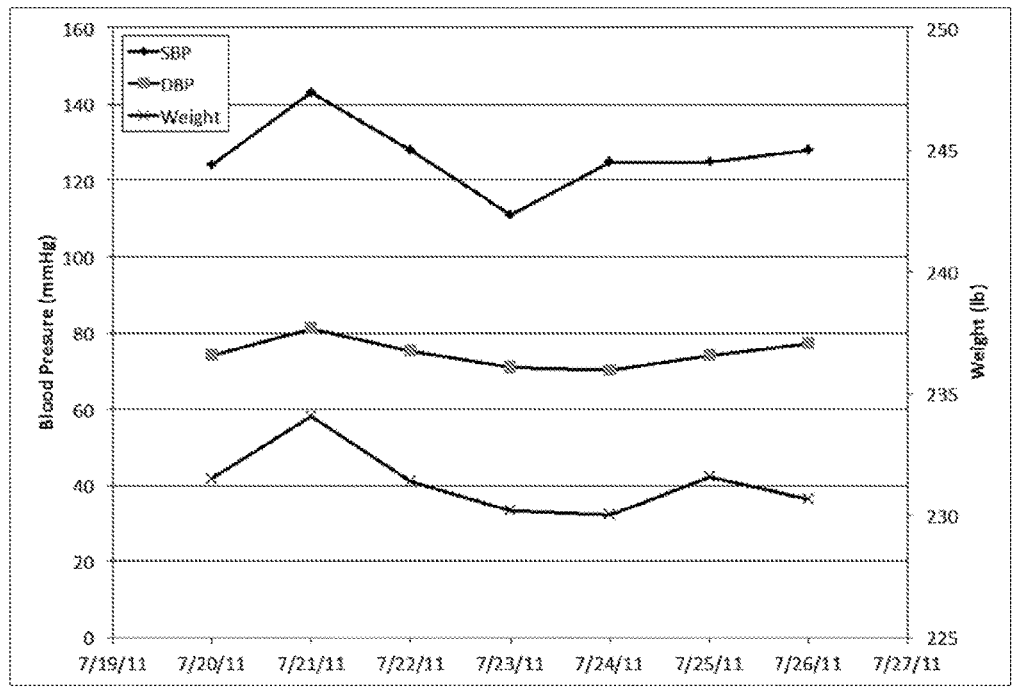
FIGS. 8A and 8B are charts that illustrate systolic and diastolic blood pressure and weight readings from a patient over two separate 7-day periods.
Figure 8B:
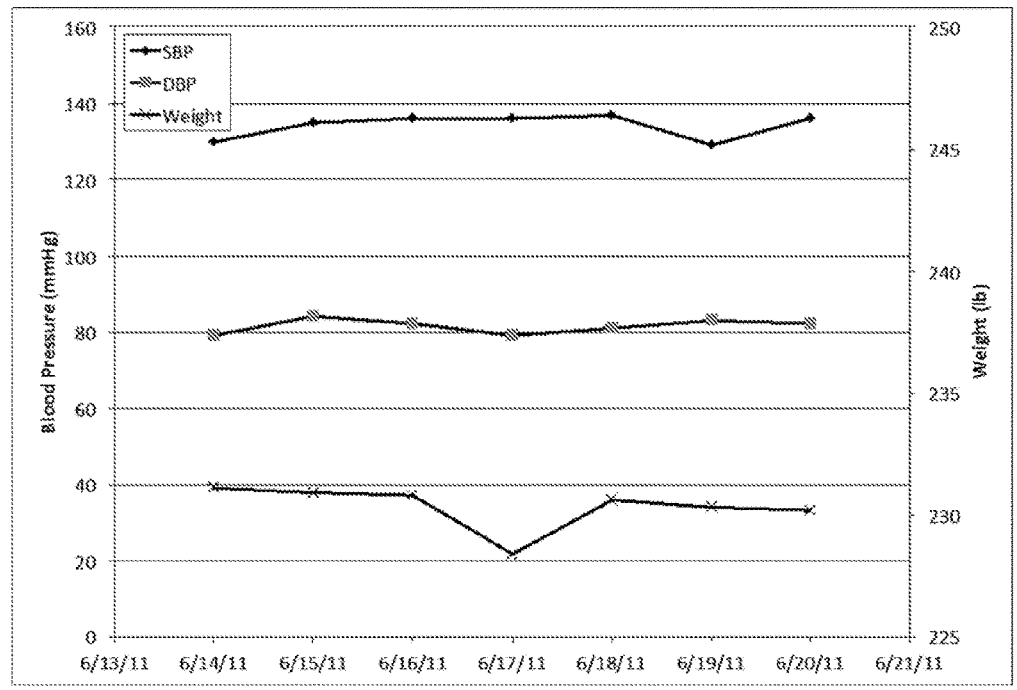

The case for using DWC as a predictor for the worsening of heart failure symptoms is further weakened from the charts illustrated in FIGS. 8A and 8B. These figures show systolic and diastolic blood pressure (SBP & DBP) and weight readings from the same patient over two separate 7-day periods. By the seventh day in FIG. 8A, the patient is known to have reported worsening of heart failure symptoms, whereas the patient reported no change in symptoms during the seven day period in FIG. 8B. Although the weight fluctuated in both cases, there is very limited change in weight (<1 lb) measured on the seventh day. If DWC were used to predict the symptom, there would most probably end up having either a large number of false positives, or the true positives would be missed altogether. On the other hand, the charts suggest that the systolic and diastolic blood pressures are less stable before the worsening of heart symptoms, suggesting that these values may serve as better predictors for this medical event.

Accordingly, for the fourth study, remote patient monitoring data was collected for study participants experiencing heart failure. The population of participants was 89% male with a mean age of approximately 54. Study participants were provided with Bluetooth weight scales, blood pressure monitors, heart rate monitors, landline or Ethernet gateways, and Android activity monitoring applications. Patients also answer a series of nine questions on a daily basis, the answers to which are interpreted to determine whether symptoms have stabilized or have worsened. These answers were crosschecked with nurses' call logs to remove any accidental false reporting. Based on these criteria there were a total of 34 instances of worsening of heart failure symptoms self-reported by nine patients during the clinical trials.

These 34 instances of worsening of heart failure symptoms were annotated in the collected data, and used to extract the positive segments. All other segments that are at least three days away from the instances were extracted as negative segments. Instances that occurred within three days of other instances were discarded. A total of nine features were extracted for each segment: daily change in systolic blood pressure, daily change in diastolic blood pressure, daily change in weight, standard deviation of systolic blood pressure over the past three days, standard deviation of diastolic blood pressure over the past three days, standard deviation of weight over the past three days, standard deviation of systolic blood pressure over the past seven days, standard deviation of diastolic blood pressure over the past seven days, and standard deviation of weight over the past seven days. Six different classifiers, listed in FIG. 5, were used. These classifiers were chosen because they utilize a wide range of fundamentally different statistical principles. This ensures that the results are based on the intrinsic discriminatory power of the extracted features rather than a particular algorithm overfitting the model. To compare, the traditional method of detecting worsening of heart failure symptoms upon detecting a DWC of two pounds was also used.

Several measures were taken to ensure the fairness of the experiments. Firstly, equal numbers of positive and negative instances were used in each experiment to prevent biasing toward a particular class. Secondly, the results were computed using ten-fold cross validation to guard against overfitting given the relatively small number of instances. Finally, each experiment was conducted ten times and the average results are reported, thus reducing the effect of outliers.

Figure 9:
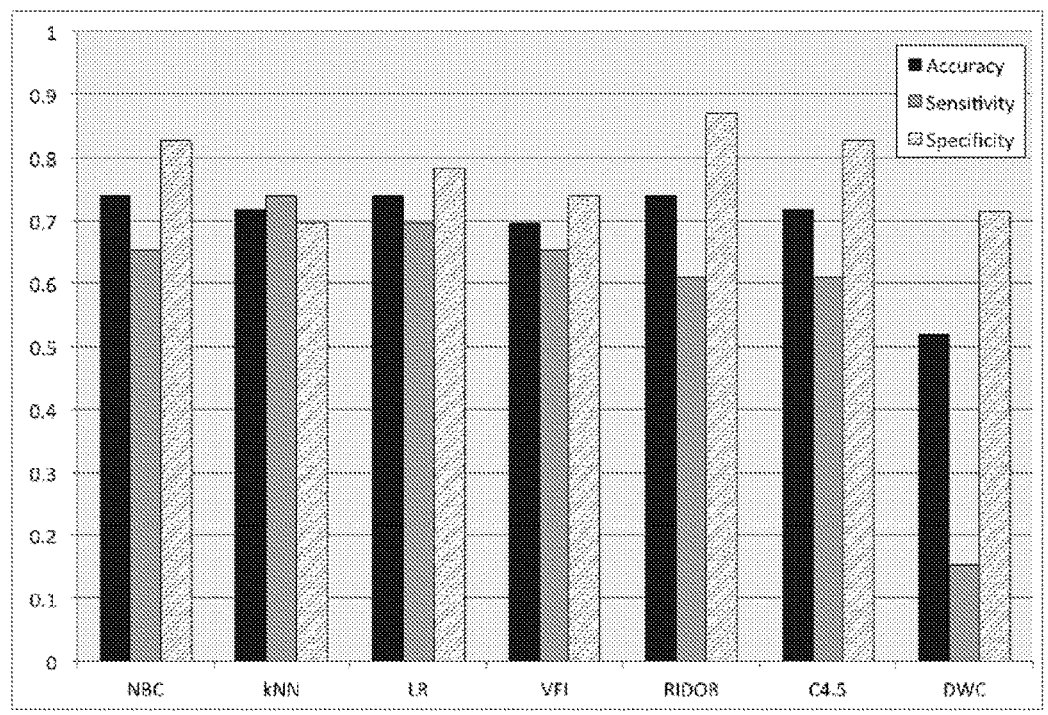
FIG. 9 is a chart that illustrates accuracy, sensitivity, and specificity for various classifiers and a daily weight change value in a test of an embodiment of the present disclosure.

The algorithms were evaluated in terms of their accuracy, sensitivity, and specificity. They are computed based on the number of True Positives (TP), True Negatives (TN), False Positives (FP), and False Negatives (FN) in the prediction results. The results for each algorithm are plotted in FIG. 4. Since the number of positive and negative instances is balanced, the minimal accuracy of any better-than-chance algorithm should be greater than 0.5. The chart in FIG. 9 shows that predicting the worsening of heart failure symptoms using DWC seems to be only marginally more accurate than guessing, with an accuracy of 0.519. This is not surprising considering that only 15.9% of the positive instances were classified as such, whereas a substantial amount of negative instances (28.6%) turn out to have a DWC of more than 2 lbs.

On the other hand, the precursor pattern detection models calculated as described above attained much higher accuracy. Three algorithms, NBC, LR, and RIDOR, were able to correctly predict the worsening or stabilization of heart failure symptoms 74% of the time. Even though VFI has the lowest accuracy of 0.696, it was still nearly 20% more accurate than DWC. Furthermore, all six algorithms had sensitivity values that were at least 45% greater than that of DWC. This suggests that the extracted features have a much stronger correlation to the worsening of heart failure symptoms than simple daily weight change, which can be further confirmed by the high specificity ranged from 0.696 (for kNN) to 0.87 (for RIDOR).

However, not all the features were equally predictive. Out of the nine features, the study determined that the classifiers consistently identify three- and seven-day standard deviations of systolic and diastolic blood pressure as the most predictive ones. Actually, C4.5, RIDOR, and LR even ignore the other features entirely when constructing the models.

Figure 10:
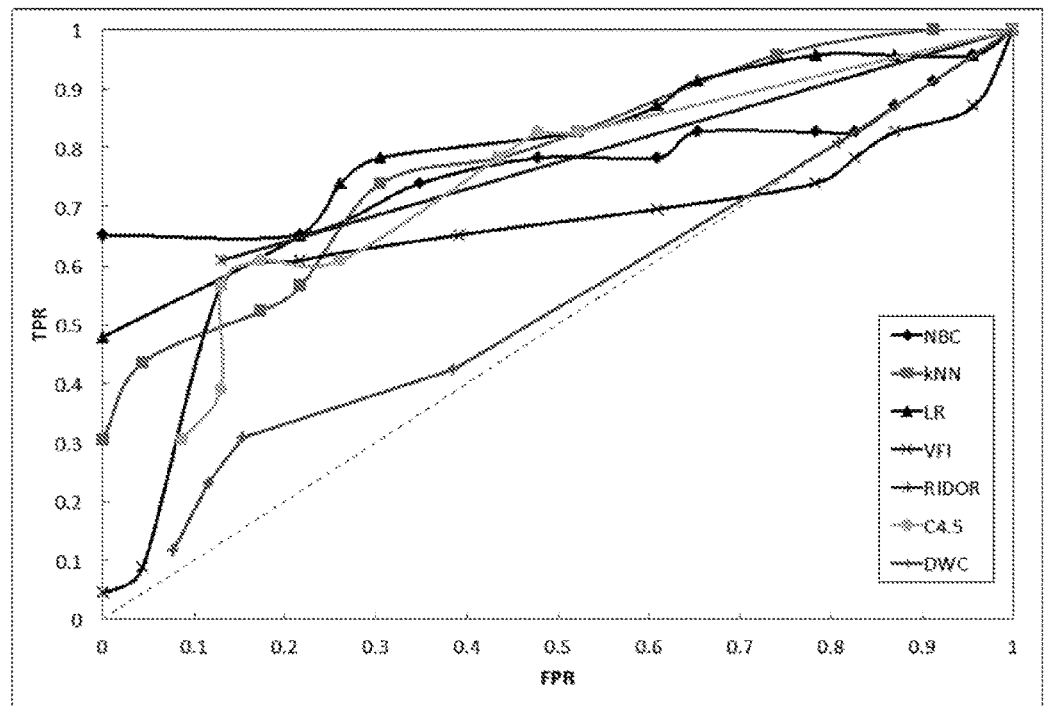
FIG. 10 is a chart that illustrates Receiver Operating Characteristic (ROC) curves for the various classifiers and the daily weight change value in the test of the embodiment of the present disclosure.

FIG. 10 is a chart that illustrates Receiver Operating Characteristic (ROC) curves for the classifiers and DWC. These curves demonstrate the effect of varying the classification algorithm's discrimination threshold on the true positive rate (TPR) vs. the false positive rate (FPR). A perfect algorithm will produce a point at the top left corner of the figure where TPR=1 and FPR=0. On the other hand, an algorithm that guesses randomly will produce a curve that follows the dotted 45-degree line in the figure where TPR=FPR. Therefore, the area under the curve (AUC) is often used as a metric to gauge the performance of a classification algorithm.

It is clear from the chart in FIG. 10 that DWC is not significantly better than random guessing. In fact, the AUC for DWC is estimated to be 0.573, which is less than 8% higher than that of a completely random guess. In comparison, the other classifiers used perform significantly better. The AUC ranged from 0.817 for LR to 0.621 for VFI. It is worth noting that NBC can be tuned to achieve a decent TPR of 0.652 while minimizing FPR to 0 at the same time. This makes NBC the most suitable algorithm to use for this particular application when the consequence of a false alarm is more costly than that of a missed prediction.

Exemplary Computing Device

Figure 11:
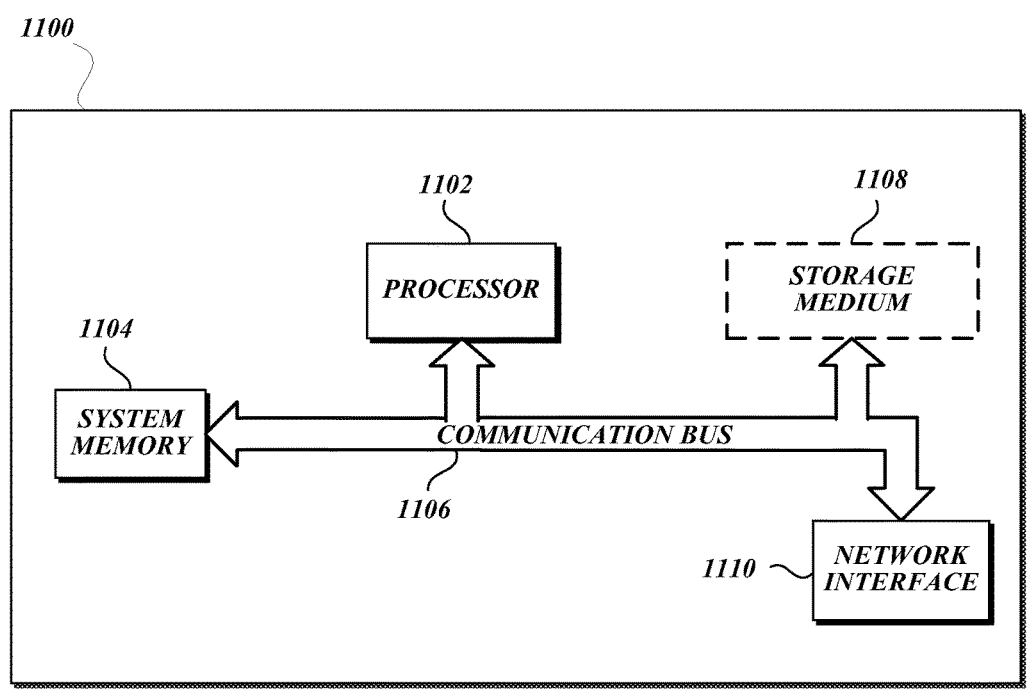
FIG. 11 is a block diagram that illustrates aspects of an exemplary computing device appropriate for use with embodiments of the present disclosure.

FIG. 11 is a block diagram that illustrates aspects of an exemplary computing device 1100 appropriate for use with embodiments of the present disclosure. While FIG. 11 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 1100 may be any one of any number of currently available or yet to be developed devices.

In its most basic configuration, the computing device 1100 includes at least one processor 1102 and a system memory 1104 connected by a communication bus 1106. Depending on the exact configuration and type of device, the system memory 1104 may be volatile or nonvolatile memory, such as read only memory ("ROM"), random access memory ("RAM"), EEPROM, flash memory, or similar memory technology. Those of ordinary skill in the art and others will recognize that system memory 1104 typically stores data and/or program modules that are immediately accessible to and/or currently being operated on by the processor 1102. In this regard, the processor 1102 may serve as a computational center of the computing device 1100 by supporting the execution of instructions.

As further illustrated in FIG. 11, the computing device 1100 may include a network interface 1110 comprising one or more components for communicating with other devices over a network. Embodiments of the present disclosure may access basic services that utilize the network interface 1110 to perform communications using common network protocols. The network interface 1110 may also include a wireless network interface configured to communicate via one or more wireless communication protocols, such as WiFi, 2G, 3G, LTE, WiMAX, Bluetooth, and/or the like.

In the exemplary embodiment depicted in FIGURE II, the computing device 1100 also includes a storage medium 1108. However, services may be accessed using a computing device that does not include means for persisting data to a local storage medium. Therefore, the storage medium 1108 depicted in FIG. 11 is represented with a dashed line to indicate that the storage medium 1108 is optional. In any event, the storage medium 1108 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data.

In this regard, the system memory 1104 and storage medium 1108 depicted in FIG. 11 are merely examples of computer-readable media.

Suitable implementations of computing devices that include a processor 1102, system memory 1104, communication bus 1106, storage medium 1108, and network interface 1110 are known and commercially available. For ease of illustration and because it is not important for an understanding of the claimed subject matter, FIG. 11 does not show some of the typical components of many computing devices. In this regard, the computing device 1100 may include input devices, such as a keyboard, keypad, mouse, microphone, touch input device, touch screen, tablet, and/or the like. Such input devices may be coupled to the computing device 1100 by wired or wireless connections including RF, infrared, serial, parallel, Bluetooth, USB, or other suitable connections protocols using wireless or physical connections. Similarly, the computing device 1100 may also include output devices such as a display, speakers, printer, etc. Since these devices are well known in the art, they are not illustrated or described further herein.

As will be appreciated by one skilled in the art, the specific routines described above in the flowcharts may represent one or more of any number of processing strategies such as event-driven, interrupt-driven, multi-tasking, multi-threading, and the like. As such, various acts or functions illustrated may be performed in the sequence illustrated, in parallel, or in some cases omitted. Likewise, the order of processing is not necessarily required to achieve the features and advantages, but is provided for ease of illustration and description. Although not explicitly illustrated, one or more of the illustrated acts or functions may be repeatedly performed depending on the particular strategy being used. Further, these FIGURES may graphically represent code to be programmed into a computer readable storage medium associated with a computing device.

While illustrative embodiments have been illustrated and described, it will be appreciated that various changes can be made therein without departing from the spirit and scope of the claimed subject matter.

The embodiments of the invention in which an exclusive property or privilege is claimed are defined as follows:

1. A computer-implemented method of generating a precursor pattern detection model for detecting an occurrence of a given type of medical event, the method comprising:
   obtaining annotated monitoring data by a computing device, wherein the annotated monitoring data represents measurements of physical conditions of at least one first patient;
   extracting, by the computing device, a set of positive segments from the annotated monitoring data, wherein each positive segment is associated with an occurrence of a medical event of the given type;
   identifying, by the computing device, a portion of the annotated monitoring data that is at least three days away from the medical events of the annotated monitoring data along a timeline;
   extracting, by the computing device, a set of negative segments from the annotated monitoring data, wherein each negative segment is not associated with an occurrence of the medical event of the given type, and wherein all of the set of negative segments are extracted from the portion of the annotated monitoring data that is at least three days away from the medical events of the annotated monitoring data along the timeline;
   executing, by the computing device, a first filter on the set of positive segments to generate a set of filtered positive segments;
   executing, by the computing device, a second filter on the set of negative segments to generate a set of filtered negative segments;
   extracting, by the computing device, a set of extracted positive features from the set of filtered positive segments and a set of extracted negative features from the set of filtered negative segments;
   selecting, by the computing device, a set of selected positive features from the set of extracted positive features and a set of selected negative features from the set of extracted negative features;
   calculating, by the computing device, the precursor pattern detection model based on the set of selected positive features and the set of selected negative features;
   storing, by the computing device on a nontransitory computer-readable medium, the precursor pattern detection model;
   sensing a signal from a second patient to form at least a portion of collected patient data;
   detecting a match between a set of the collected patient data and the precursor pattern detection model; and
   in response to the match, using the computing device and informing a party to seek or to provide medical care.

2. The computer-implemented method of claim 1, wherein the annotated monitoring data includes annotations indicating occurrences of the given medical event during collection of the monitoring data.

3. The computer-implemented method of claim 1, wherein the annotated monitoring data includes a set of signals, and the set of selected positive features includes features extracted from less than all of the set of signals included in the annotated monitoring data.

4. The computer-implemented method of claim 1, wherein executing the first filter on the set of positive segments to generate the set of filtered positive segments includes:
   executing a top-down filter on the set of positive segments to generate a set of top-down filtered positive segments; and
   executing a bottom-up filter on the set of top-down filtered positive segments to generate the set of filtered positive segments.

5. The computer-implemented method of claim 4, wherein executing the first filter on the set of positive segments to generate the set of filtered positive segments includes:
   repeatedly executing the top-down filter and the bottom-up filter until a strength of the filtered positive segments does not increase further.

6. The computer-implemented method of claim 1, wherein extracting the set of extracted positive features from the set of filtered positive segments includes performing a wavelet transform for each filtered positive segment of the set of filtered positive segments.

7. The computer-implemented method of claim 6, wherein the wavelet transform is a Haar wavelet transform.

8. The computer-implemented method of claim 1, wherein extracting the set of extracted positive features from the set of filtered positive segments includes determining a change in a value of each filtered positive segment from a value of a previous positive segment.

9. The computer-implemented method of claim 1, wherein extracting the set of extracted positive features from the set of filtered positive segments includes determining a standard deviation for each filtered positive segment.

10. The computer-implemented method of claim 1, wherein selecting the set of selected positive features from the set of extracted positive features includes selecting positive features using a wrapper procedure.

11. The computer-implemented method of claim 10, wherein selecting the positive features using the wrapper procedure includes calculating an information gain for each extracted positive feature of the set of extracted positive features.

12. The computer-implemented method of claim 11, wherein selecting the positive features using the wrapper procedure further includes selecting extracted positive features having an information gain greater than a predetermined threshold value.

13. The computer-implemented method of claim 1, wherein calculating the precursor pattern detection model based on the set of selected positive features and the set of selected negative features includes providing the set of selected positive features and the set of selected negative features as input to a classifier.

14. The computer-implemented method of claim 13, wherein the classifier is selected from a group consisting of a naïve classifier, a Bayes network classifier, a logistic regression classifier, a C4.5 decision tree classifier, a support vector machine (SVM) classifier, a voting feature: interval (VFI) classifier, and an artificial neural network (ANN) classifier.

15. The computer-implemented method of claim 1, wherein executing the first filter on the set of positive segments to generate the set of filtered positive segments includes:
for each positive segment of the set of positive segments, determining a strength of the positive segment;
subdividing the positive segment into multiple subsegments based on data granularity;
for each subsegment of the multiple subsegments, determining a strength of a remaining portion of the positive segment with the subsegment removed;
identifying a subsegment of the multiple subsegments that has a largest impact on the strength of the remaining portion of the positive segment with the subsegment removed; and
removing the identified subsegment according to the strength of the remaining portion of the positive segment with the identified subsegment removed.

16. The computer-implemented method of claim 1, wherein at least one positive segment of the set of positive segments are extracted from a portion of the annotated monitoring data before an annotated medical event of the annotated monitoring data.

17. The computer-implemented method of claim 1, wherein at least one negative segment of the set of negative segments is extracted from a portion of the annotated monitoring data associated with the least one first patient that does not exhibit or has not exhibited the medical event of the given type.

18. The computer-implemented method of claim 1, further comprising, in response to the match, causing a medication to be automatically administered, or causing an amount of monitoring to be changed.

19. A nontransitory computer-readable storage medium having instructions stored thereon, wherein the instructions are executable by at least one processor to cause the processor to perform operations comprising:
obtaining annotated monitoring data, wherein the annotated monitoring data represents measurements of physical conditions of at least one first patient;
extracting a set of positive segments from the annotated monitoring data, wherein each positive segment is associated with an occurrence of a medical event of a given type;
identifying a portion of the annotated monitoring data that is at least three days away from the medical events of the annotated monitoring data along a timeline;
extracting a set of negative segments from the annotated monitoring data, wherein each negative segment is not associated with an occurrence of the medical event of the given type, and wherein all of the set of negative segments are extracted from the portion of the annotated monitoring data that is at least three days away from the medical events of the annotated monitoring data along the timeline;
executing a first filter on the set of positive segments to generate a' set of filtered positive segments;
executing a second filter on the set of negative segments to generate a set of filtered negative segments;
extracting a set of extracted positive features from the set of filtered positive segments and a set of extracted negative features from the set of filtered negative segments;
selecting a set of selected positive features from the set of extracted positive features and a set of selected negative features from the set of extracted negative features;
calculating a precursor pattern detection model based on the set of selected positive features and the set of selected negative features;
sensing a signal from a second patient to form at least a portion of collected patient data;
detecting a match between a set of the collected patient data and the precursor pattern detection model; and
in response to the match, informing a party to seek or to provide medical care.

20. A system comprising:
at least one processor and a memory connected to the processor, the memory storing instructions executable by the processor to cause the processor to
obtain annotated monitoring data, wherein the annotated monitoring data represents measurements of physical conditions of at least one first patient;
extract a set of positive segments from the annotated monitoring data, wherein each positive segment is associated with an occurrence of a medical event of a given type;
identify a portion of the annotated monitoring data that is at least three days away from the medical events of the annotated monitoring data along a timeline;
extract a set of negative segments from the annotated monitoring data, wherein each negative segment is not associated with an occurrence of the medical event of the given type, and wherein all of the set of negative segments are extracted from the portion of the annotated monitoring data that is at least three clays away from the medical events of the annotated monitoring data along the timeline;
execute a first filter on the set of positive segments to generate a set of filtered positive segments;
execute a second filter on the set of negative segments to generate a set of filtered negative segments;
extract a set of extracted positive features from the set of filtered positive segments and a set of extracted negative features from the set of filtered negative segments;

select a set of selected positive features from the set of extracted positive features and a set of selected negative features from the set of extracted negative features;
calculate a precursor pattern detection model based on the set of selected positive features and the set of selected negative features;
sense a signal from a second patient to form at least a portion of collected patient data;
detect a match between a set of the collected patient data and the precursor pattern detection model; and
in response to the match, informed a party to seek or to provide medical care.

\* \* \* \* \*